United States Patent
Miyashita

(10) Patent No.: US 8,626,448 B2
(45) Date of Patent: *Jan. 7, 2014

(54) METHOD FOR ESTIMATING A BLOOD SUGAR CONDITION

(75) Inventor: Mariko Miyashita, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/555,562

(22) Filed: Jul. 23, 2012

(65) Prior Publication Data

US 2013/0024128 A1    Jan. 24, 2013

Related U.S. Application Data

(62) Division of application No. 12/058,778, filed on Mar. 31, 2008, now Pat. No. 8,315,808.

(30) Foreign Application Priority Data

Mar. 30, 2007    (JP) .................................. 2007-093129
Feb. 8, 2008     (JP) .................................. 2008-029717

(51) Int. Cl.
*G01N 33/48*    (2006.01)
*G01N 31/00*    (2006.01)
*G06G 7/48*     (2006.01)
*G06G 7/58*     (2006.01)

(52) U.S. Cl.
USPC .................... 702/19; 702/22; 703/11; 703/12

(58) Field of Classification Search
None
See application file for complete search history.

(56) References Cited

FOREIGN PATENT DOCUMENTS

JP    2005-342121    12/2005

*Primary Examiner* — Larry D Riggs, II
(74) *Attorney, Agent, or Firm* — Young & Thompson

(57) ABSTRACT

A blood sugar condition is estimated by measuring a urine sugar value, discriminating whether it is less than a discriminating method classification boundary value, when it is less, obtaining an averaged value of measured urine sugar values during a past predetermined period of time, measured at the same time of day as the latest measurement, calculating the difference between the averaged and measured urine sugar values, when the difference is not less than a positive discriminating reference difference, discriminating as being a blood sugar value decrease, when the measured value is not less than the discriminating method classification boundary value, obtaining an averaged value of all measured values during the past predetermined period of time, calculating a ratio between the measured and averaged values, and, when the ratio is not greater than a first discriminating reference ratio, discriminating as being the blood sugar value decrease.

14 Claims, 8 Drawing Sheets

METHOD FOR ESTIMATING A BLOOD SUGAR CONDITION

CROSS REFERENCE TO RELATED APPLICATIONS

This application is a division of co-pending application Ser. No. 12/058,778 filed on Mar. 31, 2008, which claims foreign priority to Japanese Application Nos. 2007-093129 and 2008-029717 filed on Mar. 30, 2007 and Feb. 8, 2008, respectively. The entire content of each of these applications is hereby expressly incorporated by reference.

FIELD OF INVENTION

This invention relates to a blood sugar condition estimation method and apparatus for estimating a blood sugar condition from a urine sugar measurement. In particular, this invention relates to a urine sugar condition estimation method for estimating a urine sugar condition viewed at a comparatively long span, not an instantaneous value of urine sugar value.

BACKGROUND OF INVENTION

The most important matter in medical treatment for diabetes is a blood sugar control. HbA1c (hemoglobin A1c, which is also called Glycohemoglobin) is one of indications of a blood sugar condition. HbA1c is the hemoglobin nonenzymatically combined with sugar. HbA1c is not influenced by a temporary change of blood sugar caused by meal and others. However, if a high blood sugar condition continues, the proportion of the combination rises, with the result that HbA1c becomes high. Thus, HbA1c is used as an indication of the blood sugar condition in one to two months prior to measurement, because the life of the hemoglobin is on the degree of 120 days.

Generally, a diabetic outpatient is subjected to a measurement of HbA1c in a visit to clinic of once a month, and whether the blood sugar condition is good or bad is evaluated in comparison with preceding measured values such as a measured value obtained in the latest month, etc. Based on the result of the evaluation, a policy of pharmacotherapy is discriminated, and/or a guidance for meal and exercise therapy is shown, in order to approach a normal value. Therefore, the diabetic has a very high interest in the change of HbA1c.

As a HbA1c measuring method, it is a general practice to sample blood in an medical institution and to perform a LA method (latex aggregation method) or a HPLC method (high-performance liquid chromatography method) by use of a clinical laboratory test apparatus. Incidentally, HbA1c may be measured in a medical examination, not only as an indication of the blood sugar condition but also for screening diabetes In the meanwhile, it is also possible to directly measure a blood sugar value in order to confirm the blood sugar condition. It is general that after blood is sampled in the medical institution, the blood sugar value of the sampled blood is measured by the clinical laboratory test apparatus. On the other hand, by use of a simplified blood sugar measuring device, it is possible to measure in home with no assistance of a medical professional, and an insulin using person daily utilizes the simplified blood sugar measuring device.

As mentioned above, HbA1c is a very important item as the indication of the blood sugar condition, and is very highly interesting to medical professionals and patients. However, the measurement of HbA1c has to be carried out in the medical institution. On the other hand, since HbA1c is subjected to a strong influence of a daily blood sugar value, it might be possible to estimate HbA1c on the basis of a daily blood sugar measurement. However, an "in-day" change of the daily blood sugar value is very large because of influence of meal, and therefore, a frequent measurement is required. The simplified blood sugar measuring device might be utilized to measure the daily blood sugar value, but is not convenient to the frequent measurement, because of invasion by centesis and because of a measurement cost. Therefore, it does not become a measuring method for the HbA1c estimation.

As mentioned above, a diabetic is usually blood-sampled in the medical institution monthly or bi-monthly so that the blood sugar level, HbA1c and others are measured and, if necessary, the diabetic receives a life guidance. However, it is the most desirable to the diabetic if the diabetic can know a daily blood sugar condition so that the diabetic can control the meal in accordance with the known blood sugar condition.

In the meanwhile, in comparison with the blood sugar measurement, a urine sugar measurement can be relatively easily carried out because of its non-invasiveness. In addition, it is reported that since the urine sugar measurement dynamically reflects the change of the blood sugar value exceeding a sugar elimination renal threshold, it is possible to confirm and control a high level of postcibal blood sugar on the basis of the urine sugar measurement (Non-Patent Document 1). In a conventional urine sugar measurement, a qualitative analysis using a urine sugar inspection test paper was dominant. However, the Non-Patent Document 1 is reporting that as a biochemistry measuring instrument, a urine sugar measuring device has been used which makes a quantitative measurement possible in home. The urine sugar meter as the biochemistry measuring instrument is disclosed in for example Patent Document 1 and Patent Document 2.

Non-Patent Document 1: Journal of the Takasaki Medical Association, Vol. 55, Separate Volume, pp 75-79
Patent Document 1: JP-09-297120-A
Patent Document 2: JP-2006-153849-A
Non-Patent Document 2: "DIABETES", Vol. 42, No. 11, 1999, pp 957-961
Non-Patent Document 3: "Diabetes Care", Vol. 25, No. 2, 2002, pp 275-278
Non-Patent Document 4: "Diabetes Care", Vol. 27, No. 2, 2004, pp 335-339

On the other hand, a correlation among the blood sugar value, HbA1c and the urine sugar value has been already researched (Non-Patent Document 2, Non-Patent Document 3 and Non-Patent Document 4). It is considered that if the blood sugar value rises up or falls down to become hyperglycemia in which the blood sugar value exceeds the sugar elimination renal threshold (which is generally considered to be 160 to 180 mg/dL although there is an individual difference), the urine sugar value will rise up or fall down as a matter of course. That is to say, if a risen or fallen urine sugar value continues for a considerable number of days, the blood sugar value should greatly rise up or fall down, with the result that HbA1c should correspondingly rise up or fall down after the considerable number of days. However, it is not possible to predicate how many days the risen or fallen urine sugar value is required to continue until any change appears in HbA1c, and what degree of magnitude is the actual change of HbA1c, because of a large individual difference between humans being. Similarly, because of the large individual difference, it is not possible to accurately convert a specific value $\alpha$ of the urine sugar value into a specific value $\beta$ of the blood sugar value. In the prior art, accordingly, there is no method for knowing the blood sugar value from the urine sugar value.

From a different viewpoint, even if it can be said that if a risen or fallen urine sugar value continues for a considerable number of days, the HbA1c will certainly rise up or fall down, if a warning that "the blood sugar value rose" is given after the HbA1c has actually risen, it means that the diabetic has been resultantly left in a risen blood sugar condition for the considerable number of days, and the value of the warning is not so high. Rather than to know an accurate value of HbA1c just after the measurement of the urine sugar value, it is more important to diabetics to know whether the HbA1c is in an improving tendency or in a deteriorating tendency.

In addition, focusing to the urine sugar value per se, the measured value of the urine sugar value is an instantaneous value and has a large individual difference, and considering a specific individual, the urine sugar value greatly depends upon a condition of the same individual when the measurement was carried out. Therefore, although it is possible to know the instantaneous value of the urine sugar value, it is not possible to predicate whether the urine sugar value is in an improving tendency or in a deteriorating tendency, unless the instantaneous value takes an extreme value.

SUMMARY OF INVENTION

By studying how a significant correlation between the blood sugar value and the urine sugar value just after the measurement of the urine sugar value is obtained, the inventor of this invention came to this invention.

Accordingly, an object of this invention is to evaluate and estimate a blood sugar condition from the result of a non-invasive urine sugar measurement. In particular, it is to provide a blood sugar condition estimation method and apparatus capable of indicating an improvement or a deterioration of HbA1c from a stored measurement result of the urine sugar value, by focusing to HbA1c which is one indication of the blood sugar condition and by studying the correlation between HbA1c and the urine sugar value.

In addition, another object of this invention is to evaluate a blood sugar condition or to estimate whether HbA1c is in an improving tendency or in a deteriorating tendency, from a latest urine sugar value or urine sugar values during a predetermined period including the latest urine sugar value, or alternatively to set a urine sugar value as a lifestyle improvement target and to discriminate whether or not the goal is achieved.

Still another object of this invention is to provide a urine sugar condition estimation for estimating, as an indication of a health condition, whether the urine sugar condition is in an improving tendency or alternatively in a deteriorating tendency, from a latest urine sugar value or urine sugar values during a predetermined period including the latest urine sugar value.

According to this invention, there is provided a urine sugar condition estimation method, comprising the steps of:
(1) measuring a urine sugar value A;
(2) obtaining an averaged value X of measured urine sugar values measured during a past predetermined period of time, always including all measured urine sugar values measured at the same timing in a one-day life as the timing when said latest measured urine sugar value A was measured;
(3) discriminating whether or not said measured urine sugar value A is less than a discriminating method classification boundary value;
(4) when the measured urine sugar value A is less than the discriminating method classification boundary value, calculating a difference between said averaged value X and said measured urine sugar value A;
(5) when said difference {X−A} is not less than a positive discriminating reference difference, discriminating as being a urine sugar value decrease;
(6) when the measured urine sugar value A is not less than the discriminating method classification boundary value, calculating a ratio between said measured urine sugar value A and said averaged value X; and,
(7) when said ratio {A/X} is not greater than a first discriminating reference ratio, discriminating as being the urine sugar value decrease.

More particularly, the urine sugar condition estimation method in accordance with this invention, further comprises the steps of:
(8) when said difference {X−A} is not greater than a negative discriminating reference difference, discriminating as being a urine sugar value increase;
(9) when said difference {X−A} is greater than said negative discriminating reference difference but less than said positive discriminating reference difference, discriminating as being no change in the urine sugar value;
(10) when said ratio {A/X} is not less than a second discriminating reference ratio, discriminating as being the urine sugar value increase; and
(11) when said ratio {A/X} is greater than said first discriminating reference ratio but less than said second discriminating reference ratio, discriminating as being no change in the urine sugar value.

In addition, according to this invention, there is provided a blood sugar state estimation method, comprising the steps of:
(1) measuring a urine sugar value A;
(2) obtaining an averaged value X of measured urine sugar values measured during a past predetermined period of time, always including all measured urine sugar values measured at the same timing in a one-day life as the timing when said latest measured urine sugar value A was measured;
(3) discriminating whether or not said measured urine sugar value A is less than a discriminating method classification boundary value;
(4) when the measured urine sugar value A is less than the discriminating method classification boundary value, calculating a difference between said averaged value X and said measured urine sugar value A;
(5) when said difference {X−A} is not less than a positive discriminating reference difference, discriminating as being a blood sugar value decrease;
(6) when the measured urine sugar value A is not less than the discriminating method classification boundary value, calculating a ratio between said measured urine sugar value A and said averaged value X; and,
(7) when said ratio {A/X} is not greater than a first discriminating reference ratio, discriminating as being the blood sugar value decrease.

More particularly, the blood sugar state estimation method in accordance with this invention, further comprises the steps of:
(8) when said difference {X−A} is not greater than a negative discriminating reference difference, discriminating as being a blood sugar value increase;
(9) when said difference {X−A} is greater than said negative discriminating reference difference but less than said positive discriminating reference difference, discriminating as being no change in the blood sugar value;
(10) when said ratio {A/X} is not less than a second discriminating reference ratio, discriminating as being the blood sugar value increase; and

(11) when said ratio {A/X} is greater than said first discriminating reference ratio but less than said second discriminating reference ratio, discriminating as being no change in the blood sugar value.

In the urine sugar condition estimation method and the blood sugar condition estimation method mentioned above, the passage "obtaining an averaged value X of measured urine sugar values measured during a past predetermined period of time, always including all measured urine sugar values measured at the same timing in a one-day life as the timing when said measured urine sugar value A was measured" means that the averaged value X may be obtained from only all of the measured urine sugar values measured during the past predetermined period of time at the same timing in a one-day life as the timing when said measured urine sugar value A was measured, or alternatively, from measured urine sugar values measured during the past predetermined period of time, including not only all of the measured urine sugar values measured during the past predetermined period of time at the same timing in a one-day life as the timing when said measured urine sugar value A was measured but also measured urine sugar values measured during the past predetermined period of time at a different timing or timings in a one-day life. Furthermore, for example, said discriminating method classification boundary value is 50 mg/dL, and said positive discriminating reference difference is 10 mg/dL, said negative discriminating reference difference is −10 mg/dL, said first discriminating reference ratio is 0.8, and said second discriminating reference ratio is 1.2. In addition, it is possible to select said predetermined period of time from a range of five days from five weeks.

Furthermore, according to this invention, there is provided a blood sugar state estimation method, comprising the steps of:
(1) measuring a urine sugar value A;
(2) discriminating whether or not the latest HbA1c is less than a discriminating method classification boundary value;
(3) when said latest HbA1c is less than said discriminating method classification boundary value, if said latest measured urine sugar value A was measured after a meal, obtaining an averaged value X of all post-meal measured urine sugar values measured during a past predetermined short period of time including the latest measured urine sugar value A and an averaged value Y of all post-meal measured urine sugar values measured during a past predetermined long period of time;
(4) comparing said averaged value X of the measured urine sugar values measured during said past predetermined short period of time with said averaged value Y of the measured urine sugar values measured during said past predetermined long period of time, and discriminating that a significant improvement is found if the ratio {X/Y} is not greater than a first reference value;
(5) when said latest HbA1c is not less than said discriminating method classification boundary value, obtaining an averaged value X of all measured urine sugar values measured during said past predetermined short period of time including the latest measured urine sugar value A and an averaged value Y of all measured urine sugar values measured during said past predetermined long period of time;
(6) comparing said averaged value X of the measured urine sugar values measured during said past predetermined short period of time with said averaged value Y of the measured urine sugar values measured during said past predetermined long period of time, and discriminating that a significant improvement is found if the ratio {X/Y} is not greater than said first reference value.

More particularly, the blood sugar state estimation method in accordance with this invention, further comprises the steps of:
(7) when said ratio {X/Y} is not less than a second discriminating reference ratio, discriminating that a significant deterioration is found; and
(8) when said ratio {X/Y} is greater than said first discriminating reference ratio but less than said second discriminating reference ratio, discriminating that neither the significant improvement nor the significant deterioration is found.

For example, said predetermined short period of time is not less than five days but not greater than two weeks, and said predetermined long period of time is at least two times said predetermined short period of time, and is not less than two weeks but not greater than two months. Specifically, said predetermined short period of time is one week and said predetermined long period of time is one month. In addition, the discriminating method classification boundary value of HbA1c is 9%.

Moreover, according to this invention, there is provided a blood sugar condition estimation method comprising the steps of:
(1) measuring a urine sugar value A;
(2) obtaining an averaged value X of measured urine sugar values, including the latest measured urine sugar value A, measured during a past predetermined period of time at the same timing as the timing when said latest measured urine sugar value A was measured, and considering the averaged value X thus obtained as a target value;
(3) comparing said target value, namely, said averaged value X with said latest measured urine sugar value A, and discriminating that an improvement target is achieved when the difference {X−A} is not less than 0 (zero).

Furthermore, according to this invention, there is provided a urine sugar meter (urine sugar measuring apparatus) including a microcomputer installed with a program for executing the urine sugar condition estimation method or the blood sugar condition estimation method as mentioned above.

Also, according to this invention, there is provided a personal computer installed with a program for executing the urine sugar condition estimation method or the blood sugar condition estimation method as mentioned above.

Moreover, according to this invention, there is provided a urine sugar meter (urine sugar measuring apparatus) having a function of estimating a urine sugar condition or a blood sugar condition, the urine sugar meter including at least a urine sugar value measuring means, a memory means, a clock means, an arithmetical and control means for processing information, and a display means, said arithmetical and control means operating:
(1) at each time a urine sugar value is measured by said urine sugar value measuring means, to cause a measured urine sugar value A together with a measurement day and time to be stored in said memory means;
(2) to obtain an averaged value X of measured urine sugar values stored in said memory means measured during a past predetermined period of time, always including all measured urine sugar values measured at the same timing in a one-day life as the timing when said latest measured urine sugar value A was measured;
(3) to discriminate whether or not said measured urine sugar value A is less than a discriminating method classification boundary value stored in said memory means;
(4) when the measured urine sugar value A is less than the discriminating method classification boundary value, to calculate a difference between said averaged value X and said measured urine sugar value A;

(5) when said difference {X−A} is not less than a positive discriminating reference difference stored in said memory means, to discriminate as being a urine sugar value decrease or a blood sugar value decrease and to cause said display means to display the discrimination;
(6) when the measured urine sugar value A is not less than the discriminating method classification boundary value, to calculate a ratio between said measured urine sugar value A and said averaged value X; and,
(7) when said ratio {A/X} is not greater than a first discriminating reference ratio stored in said memory means, to discriminate as being the urine sugar value decrease or the blood sugar value decrease and to cause said display means to display the discrimination.

More particularly, said arithmetical and control means further operates:
(8) when said difference {X−A} is not greater than a negative discriminating reference difference stored in said memory means, to discriminate as being a urine sugar value increase or a blood sugar value increase and to cause said display means to display the discrimination;
(9) when said difference {X−A} is greater than said negative discriminating reference difference but less than said positive discriminating reference difference, to discriminate as being no change in the urine sugar value or in the blood sugar value and to cause said display means to display the discrimination;
(10) when said ratio {A/X} is not less than a second discriminating reference ratio stored in said memory means, to discriminate as being the urine sugar value increase or the blood sugar value increase and to cause said display means to display the discrimination; and
(11) when said ratio {A/X} is greater than said first discriminating reference ratio but less than said second discriminating reference ratio, discriminating as being no change in the urine sugar value or in the blood sugar value and to cause said display means to display the discrimination.

For example, as mentioned hereinbefore, said discriminating method classification boundary value is 50 mg/dL, and said positive discriminating reference difference is 10 mg/dL, said negative discriminating reference difference is −10 mg/dL, said first discriminating reference ratio is 0.8, said second discriminating reference ratio is 1.2, and said predetermined period of time is selected from a range of five days from five weeks.

In addition, according to this invention, there is provided a urine sugar meter (urine sugar measuring apparatus) having a function of estimating a blood sugar condition, the urine sugar meter including at least a urine sugar value measuring means, a memory means, an input means through which HbA1c can be inputted, a clock means, an arithmetical and control means for processing information, and a display means, said arithmetical and control means causing the HbA1c inputted through said input means to be stored in said memory means, said arithmetical and control means operating:
(1) at each time a urine sugar value is measured by said urine sugar value measuring means, to cause a measured urine sugar value A together with a measurement day and time to be stored in said memory means;
(2) to discriminate whether or not the latest HbA1c stored in said memory means is less than a discriminating method classification boundary value stored in said memory means;
(3) when said latest HbA1c is less than said discriminating method classification boundary value, if said measured urine sugar value A was measured after a meal, to calculate an averaged value X of all post-meal measured urine sugar values stored in said memory means measured during a past predetermined short period of time including the latest measured urine sugar value A, and to calculate an averaged value Y of all post-meal measured urine sugar values measured during a past predetermined long period of time;
(4) to compare said averaged value X of the measured urine sugar values measured during said past predetermined short period of time with said averaged value Y of the measured urine sugar values measured during said past predetermined long period of time, and to discriminate that a significant improvement is found if the ratio {X/Y} is not greater than a first reference value stored in said memory means and to cause said display means to display the discrimination;
(5) when said latest HbA1c is not less than said discriminating method classification boundary value, to calculate an averaged value X of all measured urine sugar values stored in said memory means measured during said past predetermined short period of time including the latest measured urine sugar value A, and to calculate an averaged value Y of all measured urine sugar values measured during said past predetermined long period of time;
(6) to compare said averaged value X of the measured urine sugar values measured during said past predetermined short period of time with said averaged value Y of the measured urine sugar values measured during said past predetermined long period of time, and to discriminate that a significant improvement is found if the ratio {X/Y} is not greater than said first reference value and to cause said display means to display the discrimination.

More particularly, said arithmetical and control means further operates:
(7) when said ratio {X/Y} is not less than a second discriminating reference ratio stored in said memory means, to discriminate that a significant deterioration is found and to cause said display means to display the discrimination; and
(8) when said ratio {X/Y} is greater than said first discriminating reference ratio but less than said second discriminating reference ratio, to discriminate that neither the significant improvement nor the significant deterioration is found and to cause said display means to display the discrimination.

As mentioned hereinbefore, said predetermined short period of time is not less than five days but not greater than two weeks, and said predetermined long period of time is at least two times said predetermined short period of time, and is not less than two weeks but not greater than two months. Specifically, said predetermined short period of time is one week and said predetermined long period of time is one month. In addition, the discriminating method classification boundary value of HbA1c is 9%.

In addition, according to this invention, there is provided a urine sugar meter (urine sugar measuring apparatus) having a function of estimating a blood sugar condition, the urine sugar meter including at least a urine sugar value measuring means, a memory means, a clock means, an arithmetical and control means for processing information, and a display means, said arithmetical and control means operating:
(1) at each time a urine sugar value is measured by said urine sugar value measuring means, to cause a measured urine sugar value A together with a measurement day and time to be stored in said memory means;
(2) to calculate an averaged value X of measured urine sugar values stored in said memory means, including the latest measured urine sugar value A, measured during a past predetermined period of time at the same timing as the timing when said measured urine sugar value A was measured, and to consider the averaged value X thus obtained as a target value;
(3) to compare said target value, namely, said averaged value X with the latest measured urine sugar value A, and to discriminate that an improvement target is achieved when the difference {X-A} is not less than 0 (zero).

EMBODIMENTS

One embodiment of the blood sugar condition estimation method and apparatus for carrying out this invention is an improvement of the urine sugar meter (urine sugar measuring apparatus) disclosed in the above mentioned Patent Document 2, as one example of biochemistry measuring instrument, configured to detect the urine sugar by use of an action of enzyme. Accordingly, a fundamental construction and function are the same as the urine sugar meter disclosed in the above mentioned Patent Document 2. Thus, the contents of Patent Document 2 are incorporated by reference in its entirety into this application, and a detailed description will be omitted.

Figure 1:
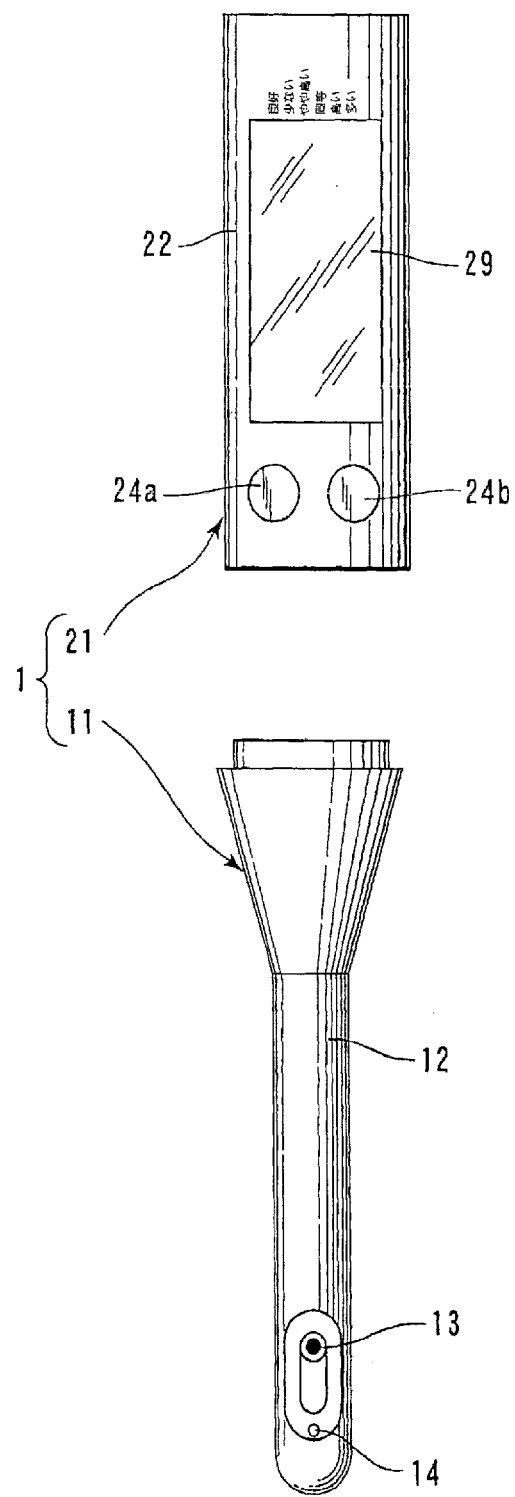
FIG. 1 is an appearance view of a conventional urine sugar meter in a separated condition.
Figure 2:
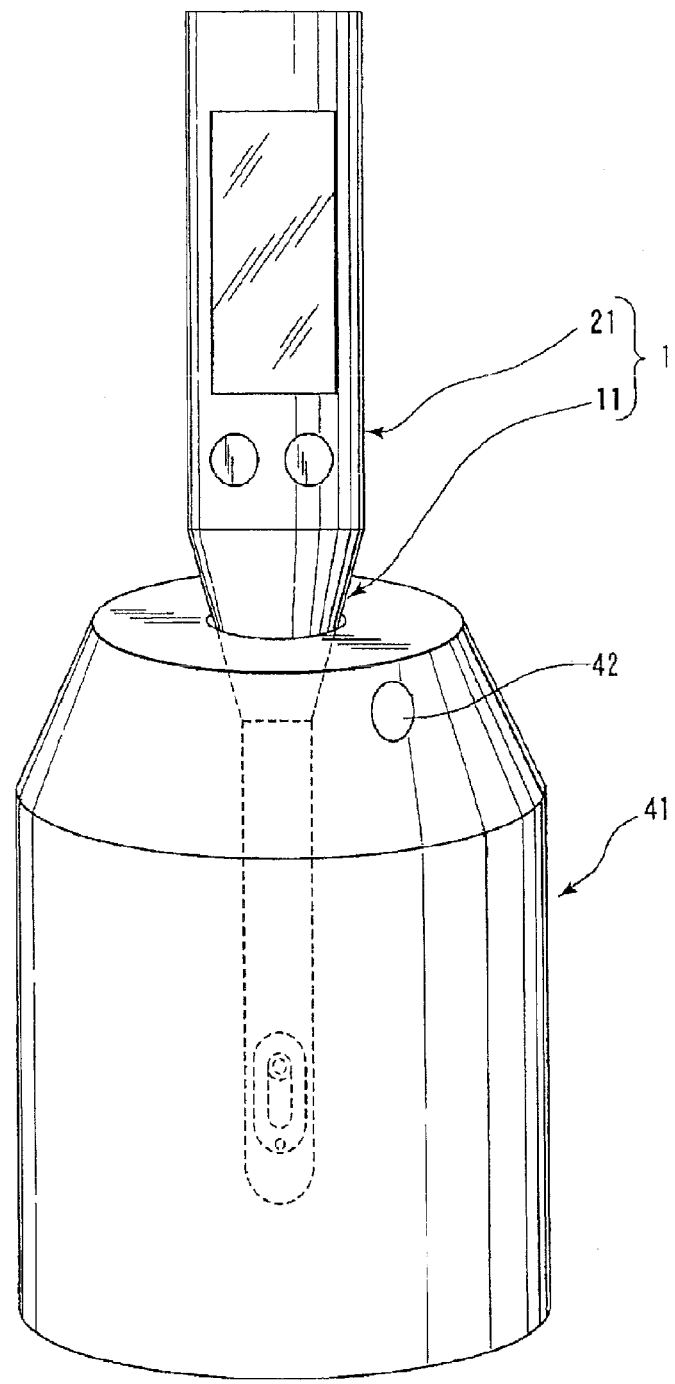
FIG. 2 is an appearance view of the conventional urine sugar meter in a repository condition.
Figure 3:
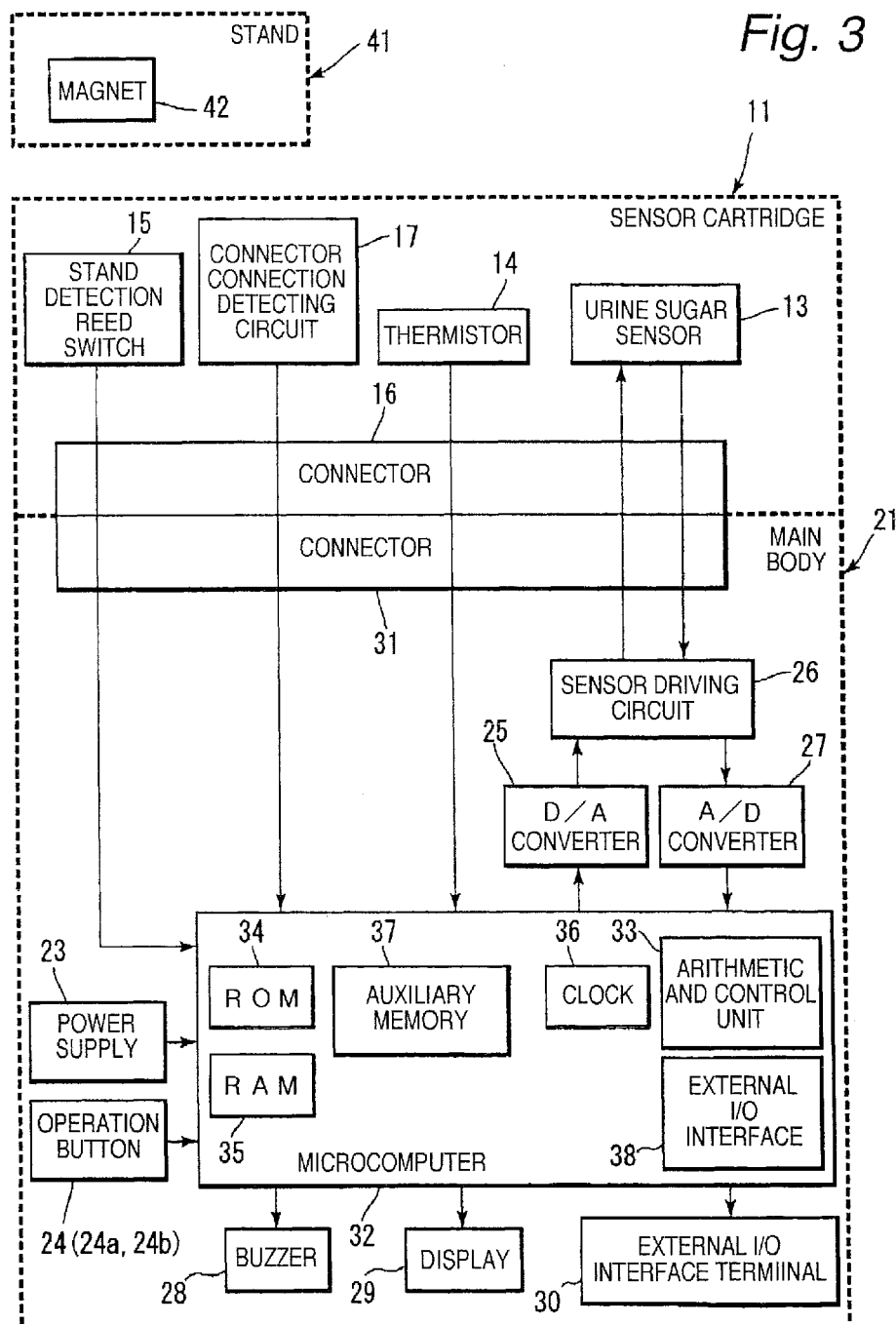
FIG. 3 is a block diagram showing an electronic construction of the conventional urine sugar meter.
Figure 4:
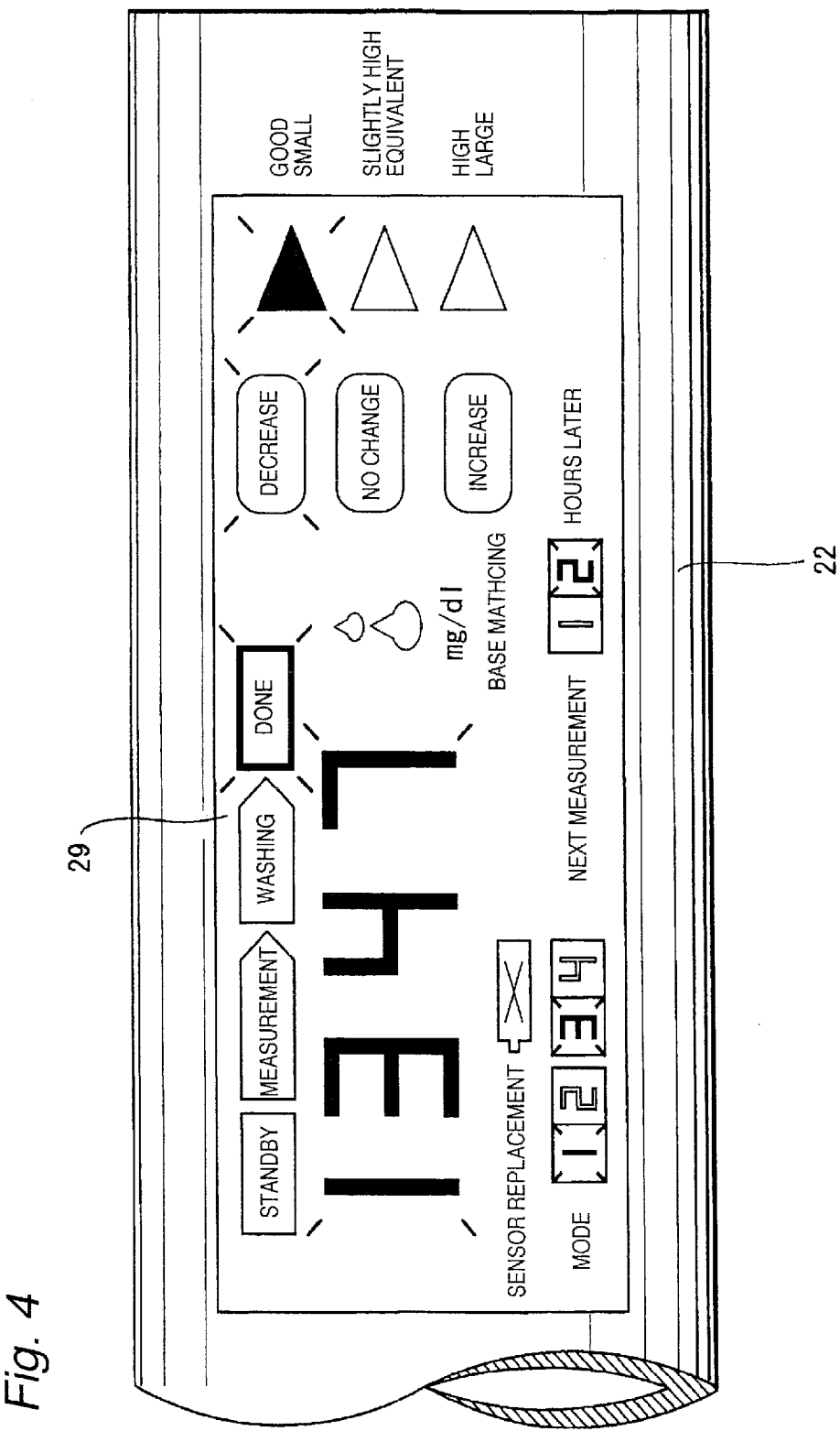
FIG. 4 is a view illustrating a display condition in a display section of the urine sugar meter shown in FIG. 1.

FIGS. 1 and 2 are an appearance view, FIG. 3 is a block diagram illustrating an electrical construction, and FIG. 4 is a partial enlarged view showing the display form of a display section.

As shown in FIG. 1, the shown urine sugar meter (urine sugar measuring apparatus) 1 comprises a sensor cartridge 11 for electrochemically detecting sugar in the urine, and a meter main body 21 which serves as a grip for holding the urine sugar meter during measurement and which measures and displays the concentration of sugar in the urine based on the detection made by the sensor cartridge 11. In order to make the sensor cartridge 11 exchangeable, the sensor cartridge 11 and the meter main body 21 can be separated from each other as shown in FIG. 1 and can be coupled with each other as shown in FIG. 2. Incidentally, as shown in FIG. 1, the urine sugar meter 1 is so configured that the urine sugar meter 1 can be inserted and stored in a stand 41 having a magnet 42, when it is not used.

The sensor cartridge 11 comprises a urine sugar sensor 13, a thermistor 14, a stand detection reed switch 15, a connector 16, and a connector connection detection circuit 17, as shown in the block diagram of FIG. 3, which are accommodated within a housing 12 shown in FIG. 1. In addition, the meter main body 21 comprises a power supply 23, operation buttons 24 (24a, 24b), a D/A (digital-to-analog) converter 25, a sensor driving circuit 26, an A/D (analog-to-digital) converter 27, a buzzer 28, a LCD (liquid crystal display) display 29, an external I/O (input-output) interface terminal 30, a connector 31, and a microcomputer 32, which are accommodated within a housing 22.

The urine sugar sensor 13 has a lifetime, and when it reaches a use limit, a "sensor exchange" is indicated in the LCD display 29. In such a case, a user detaches the sensor cartridge 11 from the meter main body 21, and attaches a new sensor cartridge 11 to the meter main body 21. The sensor cartridge 11 and the meter main body 21 are then electrically interconnected, and therefore, it is preferred that when the sensor cartridge 11 is exchanged, it is possible to easily connect the connector 16 of the sensor cartridge 11 to the connector 31 of the meter main body 21. Additionally, since the sensor cartridge 11 is bathed with urine and a washing water, a boundary between the sensor cartridge 11 and the meter main body 21 has to be excellent in a waterproof property, and the waterproof property has to be always maintained irrespectively of how many time it is exchanged.

When the life of the battery contained in the meter main body 21 has terminated, it is necessary to replace the battery with a new battery. Therefore, attention should be preferably paid so that the user can easily make the exchange of battery. That is to say, it is preferred that the battery can be easily taken out from the meter main body 21 and then the new battery can be easily mounted in the meter main body 21.

The urine sugar sensor 13 detects the concentration of sugar in the urine over a wide range from a low level to a middle level and to a high level, while excluding the influence of foreign substances in the urine. The urine sugar sensor 13 is to utilize enzyme as a sensor for the urinary constituent detection. The thermistor 14 detects the temperature of the urine at the time of measurement in order to compensate for the temperature characteristics of the urine sugar sensor 13.

When the urine sugar meter 1 is located in the stand 41, the stand detecting reed switch 15 is put in an OFF condition (or, ON condition) by action of a magnetic field of the magnet 42. Recognizing the OFF condition (or, ON condition) of the stand detecting reed switch 15, the microcomputer 32 puts the LCD display 29 into an OFF condition in order to reduce an electric power consumption to the utmost, and also, the microcomputer 32 itself becomes a sleep condition, excepting for a counting function and a function for monitoring the stand detecting reed switch 15. If the urine sugar meter 1 is taken out from the stand 41, the stand detecting reed switch 15 is moved out of the extent of the influence of the magnetic field of the magnet 42, with the result that the stand detecting reed switch 15 is put into the ON condition (or, OFF condition). Recognizing the ON condition (or, OFF condition) of the stand detecting reed switch 15, the microcomputer 32 recovers all the functions of the urine sugar meter so that a mode setting, calibration and the measurement of the urinary sugar concentration become possible.

The power supply 23 is a battery and supplies an electric power to various electrical systems of the urine sugar meter 1. The operation buttons 24 (24a and 24b) detect a depression thereof, and are used by a user to select, set and register a mode or a meal menu or correct a meal menu. The D/A converter 25 converts a digital signal (driving signal) from the microcomputer 32 into an analog signal (driving signal), and outputs the analog signal thus obtained. On the basis of the driving signal from the D/A converter 25, the sensor driving circuit 26 supplies a driving signal to the urine sugar sensor 13, and receives a detection signal detected by the urine sugar sensor 13 to supply the received detection signal to the A/D converter 27.

The A/D converter 27 converts the analog signal (detection signal) from the sensor driving circuit 26 into a digital signal (detection signal), and outputs the digital signal thus obtained. On the basis of a signal from the microcomputer 32, the buzzer 28 generates a buzzer sound for notifying a start of the urine sugar measurement, for example. Based on a signal from the microcomputer 32, the LCD display 29 displays the status of the calibration, the status of the measurement, the notification of the sensor exchange, the notification of the battery exchange, the status of the selection mode, a preliminary announcement of the next measurement, the indication of the result of the urine sugar measurement, and the notification of the result of the discrimination.

More specifically, the display 29 displays the status of calibration by lighting the "reference matching (base matching)" and the "droplet marks" of display items shown in FIG. 4 at the time of calibration. Further, the display 29 displays the status of measurement by lighting any of "standby", "measuring", "cleaning" and "done" in the course of the measurement. Also, the display 29 displays the notification of replacement of the sensor cartridge 11 by lighting the "sensor replacement" when the urine sugar sensor 13 is to be replaced. In addition, the display 29 displays the notification of replacement of the battery by lighting the "battery mark" when the battery is to be replaced. Further, the display 29 displays the status of selected mode by lighting the "mode" and a selected one of "1", "2", "3" and "4" adjacent to the "mode" at the time of event, in order to indicate the status of the selected mode. Also, the display 29 displays the preliminary announcement of the next measurement by lighting the "next measurement" and "hours later", and "1" or "2" therebetween at the time of event. Further, the display 29 displays the indication of the urine sugar measurement result by lighting a urine sugar change value, a reference urine sugar change value or a normal urine sugar change value in "4-digit number" exemplified as "1347" at the center of the drawing, after measurement, respectively. Further, the display 29 displays the status of the selected mode by lighting one of three "triangle marks" which corresponds in position to one of discrimination contents printed on the housing 22 after each discrimination.

In addition, one of "decrease", "no change" and "increase" is lit depending upon whether the urine sugar value decreases, does not change, or increases.

The external input-output interface terminal 30 is to connect the external input-output interface 38 in the microcomputer 32 with an external apparatus such as a personal computer or the like (shown in the conceptual view of FIG. 9), in order to enable communication of various data (input data from the external apparatus, and output data such as a urine sugar measurement result and a discrimination result from the urine sugar meter 1) between the microcomputer 32 and the external apparatus. The connector 16 and 31 electrically interconnect between the sensor cartridge 11 and the meter main body 21. The connector connection detecting circuit 17 detects whether the connectors 16 and 31 are maintained in a connection condition.

Similarly to Patent Document 2 mentioned hereinbefore, the microcomputer 32 comprises an arithmetic and control unit 33 for executing various urine sugar value computations and various "good or bad" discriminations and for performing various controls, a ROM 34 for storing programs for controls and computations, a RAM 35 for temporarily storing the computation results, programs read from an external device, and the like, a clock 36 for generating a clock signal for various notifications, an auxiliary memory 37 for storing the selected mode, the meal menus, various computed urine sugar values and various discrimination results until they are updated, an external I/O interface 38 for communicating various data (i.e. input data from an external device and output data such as urine sugar measurement results and discrimination results from the urine sugar meter 1) between an external device such as a personal computer and the urine sugar meter 1, and various ports (not shown) connected to various electrical systems. The microcomputer 32 notifies a user that an immediately-before-meal urine sugar value, an after-meal urine sugar value, a reference before-meal urine sugar value, a reference after-meal urine sugar value, a normal before-meal urine sugar value and a normal after-meal urine sugar value should be measured. The microcomputer 32 also performs measurement of the before-meal urine sugar value, the immediately-before-meal urine sugar value, the after-meal urine sugar value, the reference before-meal urine sugar value, the immediately-before-meal urine sugar value, the reference after-meal urine sugar value, the normal before-meal urine sugar value, a normal immediately-before-meal urine sugar value and the normal after-meal urine sugar value. The microcomputer 32 further performs computation of a urine sugar change value (difference between the after-meal urine sugar value and the immediately-before-meal urine sugar value), a reference urine sugar change value (difference between the reference after-meal urine sugar value and the reference immediately-before-meal urine sugar value), a normal urine sugar change value (difference between the normal after-meal urine sugar value and the normal immediately-before-meal urine sugar value), and a meal difference urine sugar change value (difference between the normal urine sugar change value and the reference urine sugar change value), The microcomputer 32 also discriminates on the basis of the urine sugar change value whether a change in sugar amount within a body of a human being is good or bad, and discriminates on the basis of the meal difference urine sugar change value whether the content of the normal meal menu is good or bad. Furthermore, the microcomputer 32 performs processing such as a control of the output of the results of the computations and the discriminations as mentioned above.

In addition, according to this invention, the microcomputer 32 discriminates on the basis of the latest measurement result of the urine sugar value whether the blood sugar value decreases, does not change or increases, and then, lights one of the "decrease", "no change" and "increase" of the display unit, based on the result of the discrimination.

Now, an operation of this invention will be described. But, since the measuring method itself of the urine sugar value and the method for obtaining the various values mentioned above are explained in detail in Patent Documents 1 and 2 mentioned hereinbefore, the contents of Patent Documents 1 and 2 are incorporated by reference in its entirety into this application, and a detailed description will be omitted.

Embodiment 1

Comparison and Discrimination with One-Week Average

Figure 5:
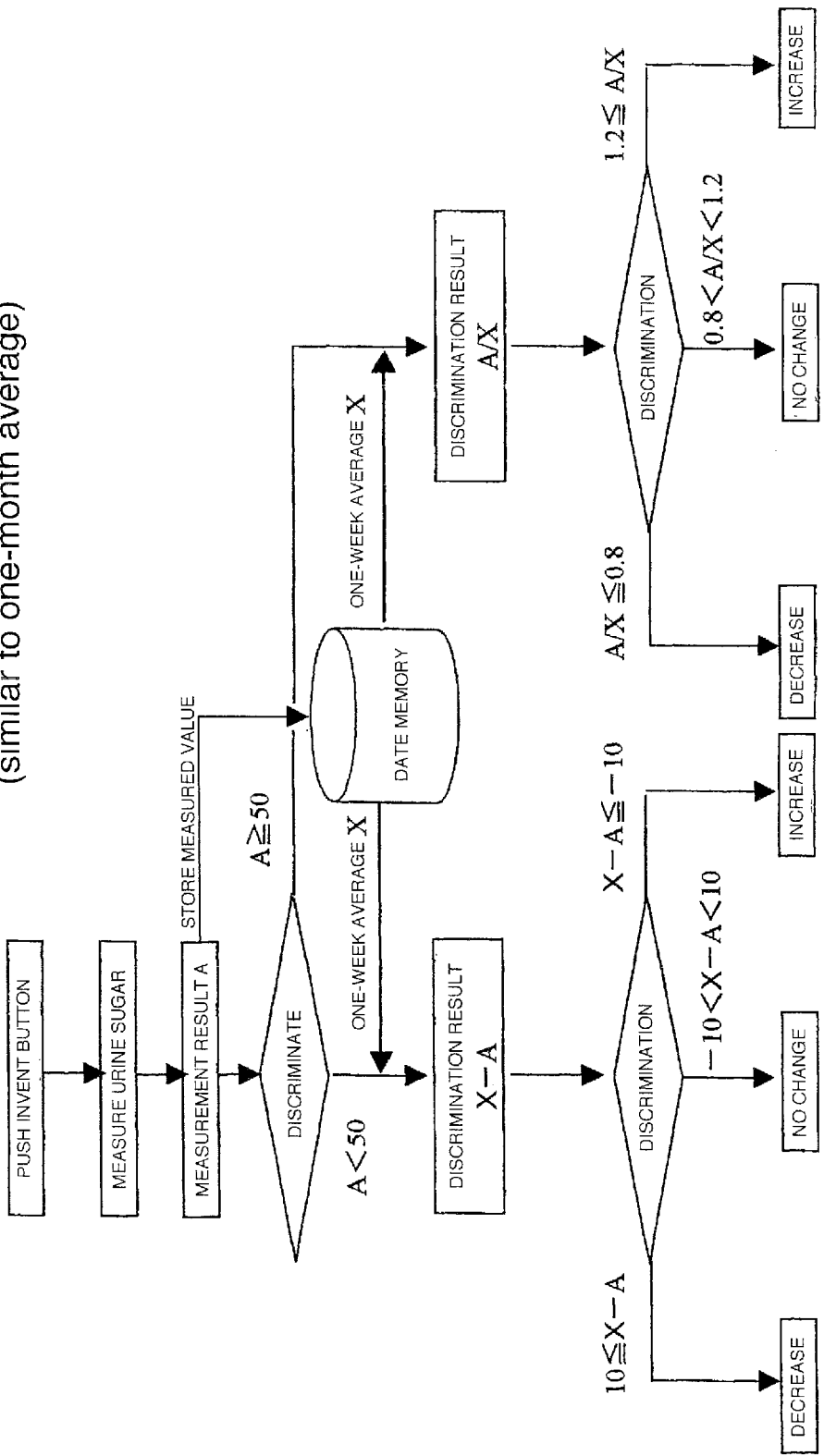
FIG. 5 is a flowchart illustrating the procedure of the blood sugar condition estimation method in accordance with the Embodiment 1 and the Embodiment 2 of this invention.

By comparing the latest measured urine sugar value with measured urine sugar values in the past one week, whether the latest blood sugar condition is good or bad is discriminated. FIG. 5 is a flowchart of the procedure of Embodiment 1. However, since the procedure of Embodiment 1 is the same as the procedure of Embodiment 2 which will be described hereinafter, what should be indicated as "Xw" in Embodiment 1 and what should be indicated as Xm in Embodiment 2 are indicated merely as "X" in the flowchart of FIG. 5. The urine sugar meter 1 stores the measured urine sugar data in at least the past one week together with respective measurement timings in the auxiliary memory 37 of the microcomputer 32.

By using the urine sugar meter 1 and by pushing a measurement start button on the urine sugar meter 1, the urine sugar is measured. The microcomputer 32 of the urine sugar meter 1 stores the measurement timing together with the measurement data in the auxiliary memory 37.

First of all, the microcomputer 32 discriminates whether or note the latest measured urine sugar value A is less than 50 mg/dL.

When the latest measured urine sugar value A is less than 50 mg/dL, the microcomputer 32 reads out all measured urine sugar values in the past one week at the same timing (such as before-meal or after-meal) in a one-day life as the timing when the latest measured urine sugar value A was measured (here, the same timing should be considered not to require the accuracy in units of minute, such as how many minutes before or after meal, and this will be applied in the following descriptions). Furthermore, the microcomputer 32 calculates an averaged value Xw of the read-out measured urine sugar values in the past one week, and then, calculates a difference between the one-week averaged value Xw and the latest measured urine sugar value A, namely, {Xw−A}, and further discriminates whether or not {Xw−A} is not less than 10 mg/dL and whether or not {Xw−A} is not greater than −10 mg/dL.

When {Xw−A} is not less than 10 mg/dL, the "decrease" of the display is lit. When {Xw−A} is not greater than −10 mg/dL, the "increase" of the display is lit. Otherwise, namely, when −10 mg/dL<{Xw−A}<10 mg/dL, the "no change" of the display is lit.

When the latest measured urine sugar value A is not less than 50 mg/dL, the microcomputer calculates the ratio between the latest urine sugar value A and the one-week averaged value Xw obtained as mentioned above (namely, A/Xw), and then, discriminates whether or not {A/Xw} is not greater than 0.8 and whether or not {A/Xw} is not less than 1.2.

When {A/Xw} is not greater than 0.8, the "decrease" of the display is lit. When whether or not {A/Xw} is not less than 1.2, the "increase" of the display is lit. Otherwise, namely, when 0.8<{A/Xw}<1.2, the "no change" of the display is lit.

Embodiment 2

Comparison and Discrimination with One-Month Average

By comparing the latest measured urine sugar value with measured urine sugar values in the past one month, whether the latest blood sugar condition is good or bad is discriminated. As mentioned hereinbefore, the procedure is the same as the flowchart of the procedure of Embodiment 1 as shown in FIG. 5.

In case of this Embodiment 2, the urine sugar meter 1 stores the measurement data of the urine sugar value in at least the past one month together with respective measurement timings in the auxiliary memory 37 of the microcomputer 32. By using the urine sugar meter 1 and by pushing the measurement start button of the urine sugar meter 1, the urine sugar is measured. The microcomputer 32 of the urine sugar meter 1 stores the measurement timing together with the measurement data in the auxiliary memory 37.

First of all, the microcomputer 32 discriminates whether or note the latest measured urine sugar value A is less than 50 mg/dL.

When the latest measured urine sugar value A is less than 50 mg/dL, the microcomputer 32 reads out all measured urine sugar values in the past one month at the same timing in a one-day life as the timing when the latest measured urine sugar value A was measured, and then, calculates a one-month averaged value Xm. The microcomputer 32 calculates a difference between the one-month averaged value Xm and the latest measured urine sugar value A, namely, {Xm−A}, and further discriminates whether or not {Xm−A} is not less than 10 mg/dL and whether or not {Xm−A} is not greater than −10 mg/dL.

When {Xm−A} is not less than 10 mg/dL, the "decrease" of the display is lit. When {Xm−A} is not greater than −10 mg/dL, the "increase" of the display is lit. Otherwise, namely, when −10 mg/dL<{Xm−A}<10 mg/dL, the "no change" of the display is lit.

When the latest measured urine sugar value A is not less than 50 mg/dL, the microcomputer calculates the ratio between the latest urine sugar value A and the one-month averaged value Xm obtained as mentioned above (namely, A/Xm), and then, discriminates whether or not {A/Xm} is not greater than 0.8 and whether or not {A/Xm} is not less than 1.2.

When {A/Xm} is not greater than 0.8, the "decrease" of the display is lit. When whether or not {A/Xm} is not less than 1.2, the "increase" of the display is lit. Otherwise, namely, when 0.8<{A/Xm}<1.2, the "no change" of the display is lit.

In Embodiment 1 and Embodiment 2 mentioned above, when the latest urine sugar value is less than 50 mg/dL, the discrimination is carried out by obtaining the difference between the latest measured value and the averaged value in the past, and when the latest urine sugar value is not less than 50 mg/dL, the discrimination is carried out by obtaining the ratio between the latest measured value and the averaged value in the past. However, the boundary value of the urine sugar value for classifying the discriminating method is in no way limited to 50 mg/dL. In addition, in Embodiment 2, the one-month averaged value Xm is obtained by reading out all the measured urine sugar values in the past one month at the same timing in a one-day life as the timing when the latest measurement was performed. However, it is possible to obtain the one-month averaged value Xm by reading out all the measured urine sugar values in the past one month, if the read-out measured urine sugar values includes all the measured urine sugar values in the past one month at the same timing in a one-day life as the timing when the latest measurement was performed, even if the read-out measured urine sugar values includes measured urine sugar values obtained at other timings. The reason for this is that the influence of variation in measured urine sugar values attributable to different measurement timings is considered to be slight.

The urine sugar value takes the wide value from a value less than 50 mg/dL to a value reaching thousands mg/dL. When the urine sugar value is less than 50 mg/dL, whether or not the difference between the latest measured value and the averaged value of the past measured values is less than 10 mg/dL has an important meaning, but in the case that the urine sugar value reaches thousands mg/dL, if the difference between the latest measured value and the averaged value of the past measured values is less than 10 mg/dL, the difference would be negligible in view of significant digites. Accordingly, when the urine sugar value is large, considering the case of performing the discrimination on the basis of the difference between the latest measured value and the averaged value of the past measured values, it would be necessary to classify, depending upon the magnitude of the measured urine sugar value, the difference that becomes the reference for discriminating whether it is improvement or deterioration, for example into a first case that the measured urine sugar value is 50 mg/dL to 100 mg/dL, a second case that the measured urine sugar value is 100 mg/dL to 300 mg/dL, a third case that the measured urine sugar value is 300 mg/dL to 1000 mg/dL, a fourth case that the measured urine sugar value is 1000 mg/dL to 3000 mg/dL, and a fifth case that the measured urine sugar value is not less than 3000 mg/dL. This is very troublesome. Therefore, the 50 mg/dL of the discriminating method classification boundary value in Embodiment 1 and in Embodiment 2 is not a critical value.

In the case of adopting the two different discriminating methods as in Embodiment 1 and Embodiment 2, the discriminating method classification boundary value of the urine sugar value can be selected from the range of 30 mg/dL to 100 mg/dL. In addition, the difference that becomes the reference for discriminating whether it is improvement or deterioration, can be varied, depending upon the discriminating method classification boundary value of the urine sugar value. However, it is now considered to have the highest validity that the discriminating method classification boundary value of the urine sugar value is 50 mg/dL and the difference that becomes the reference for discriminating whether it is improvement or deterioration, is 10 mg/dL.

Embodiment 3

Estimation Method of the Urine Sugar Condition

The control of health condition is required by not only diabetics but also humans being who are not a diabetic. Apart from the correlation among the blood sugar value, HbA1c and the urine sugar value, a rise of the urine sugar value is not desirable for not only diabetics but also healthy humans being. However, there is a dispersion in the measured value of the urine sugar value, namely, in the instantaneous value of the urine sugar value, and in particular, the urine sugar value greatly changes depending upon the content of meal. Therefore, the urine sugar value does not directly become an index of the health condition. As such, it is difficult to grasp from a one-time measurement a "variation in time in a long or middle span" which can constitute a substantially health index. Furthermore, since the instantaneous value of the urine sugar value has a large dispersion as mentioned above, even if the urine sugar values are simply plotted in a graph over a long or middle span, it is difficult to grasp the variation in time of the urine sugar values, and therefore, it is not sufficient as the health index. From a different viewpoint, it is required for not only diabetics but also healthy humans being, to know whether or the health condition is now in an improving tendency or in a deteriorating tendency from the viewpoint of a relatively longe span, not becoming optimistic or pessimistic dependently upon the urine sugar value obtained from a one-time measurement. Examining the methods of Embodiment 1 and Embodiment 2 mentioned above from this viewpoint, if the urine sugar value is discriminated in accordance with the methods of Embodiment 1 and Embodiment 2, it will become an indication of the health condition. Accordingly, the above mentioned blood sugar condition estimation method will become a urine sugar condition estimation method without modification.

Embodiment 4

HbA1c Estimation

Figure 9:
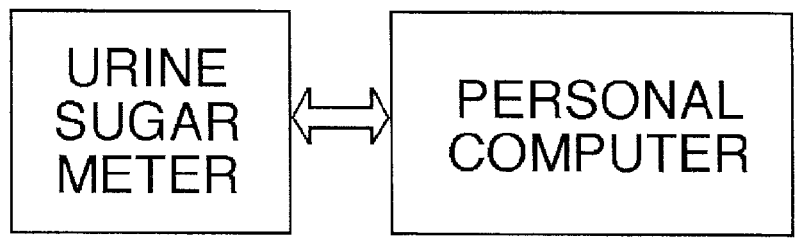
FIG. 9 is a block diagram illustrating a connection between the urine sugar meter and a personal computer.

The urine sugar meter 1 is so configured to connect to an external personal computer, as shown in the conceptual scheme of FIG. 9. Therefore, the urine sugar meter 1 can be connected with the personal computer, and by operating the personal computer, HbA1c can be written and stored in the auxiliary memory 37 of the microcomputer 32 of the urine sugar meter. This facilitates to compare between HbA1c and the urine sugar value. In the meanwhile, the urine sugar meter 1 stores the measurement data of the urine sugar value in at least the past one month together with respective measurement timings in the auxiliary memory 37 of the microcomputer 32.

Figure 6:
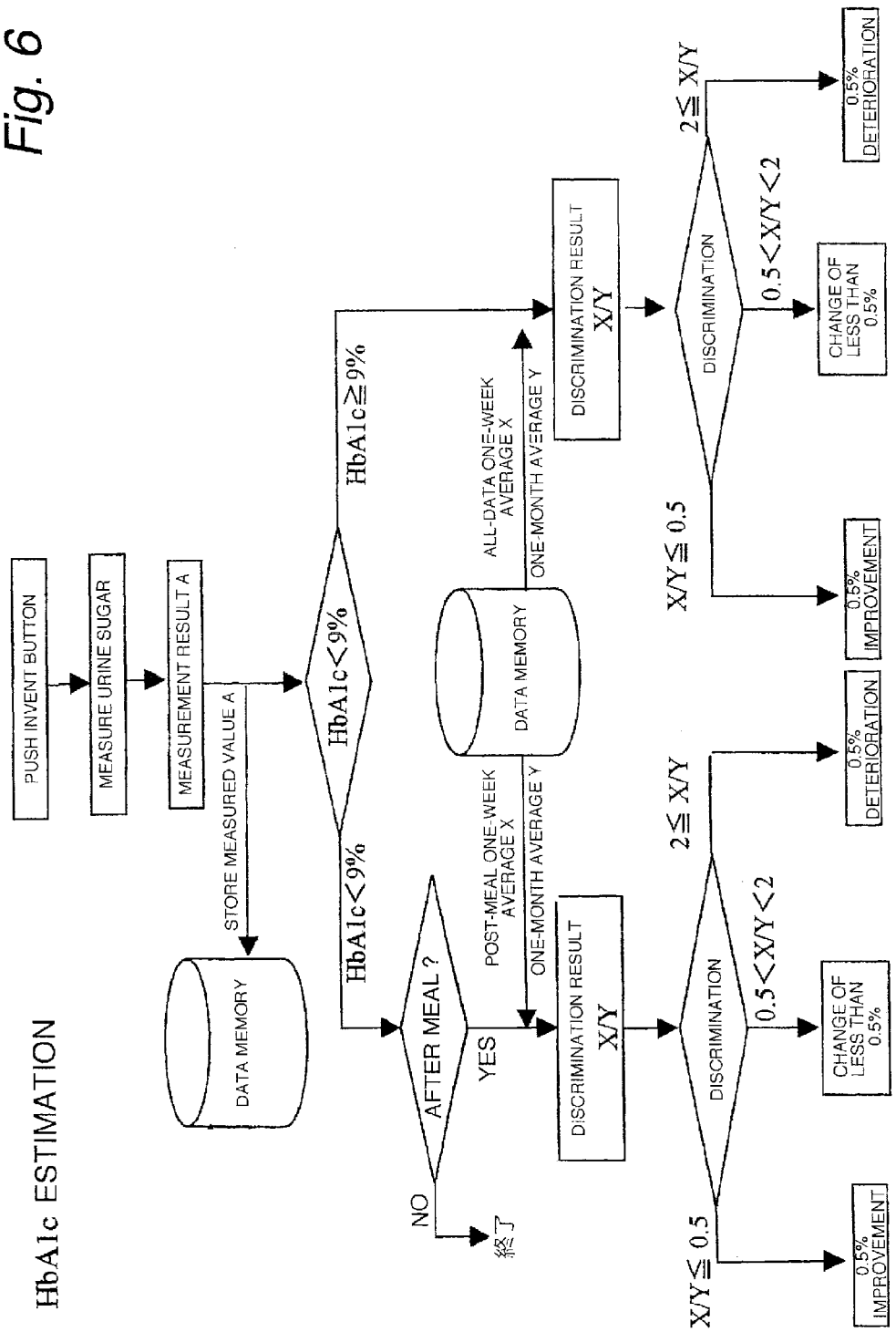
FIG. 6 is a flowchart illustrating the procedure of the blood sugar condition estimation method in accordance with the Embodiment 4 of this invention.

FIG. 6 is a flowchart of the procedure for estimating whether or HbA1c is in an improving tendency in a deteriorating tendency, by comparing the present blood sugar condition considered from the urine sugar value with the past blood sugar condition considered from the urine sugar values.

First of all, after HbA1c is measured, the urine sugar meter 1 is connected with the personal computer, and HbA1c is written and is written and stored in the auxiliary memory 37 of the microcomputer 32 of the urine sugar meter, by operating the personal computer.

In the meanwhile, the measurement data of the urine sugar values in at least the past one month before the latest HbA1c was written in the auxiliary memory 37 of the microcomputer 32 is stored together with respective measurement timings in the auxiliary memory 37 of the microcomputer 32.

(1) At each time urine sugar value is measured by the urine sugar meter 1, the measurement result A is stored in the auxiliary memory 37 of the microcomputer 32.

(2) At each time the urine sugar value measurement result A is stored in the auxiliary memory 37 of the microcomputers 32, whether or not the latest HbA1c stored in the auxiliary memory 37 is less than 9% is discriminated. If the latest HbA1c is less than 9%, whether or not the latest measurement result A of the urine sugar value is an after-meal data is discriminated. If the latest measurement result A is not an after-meal data, the processing terminates. The following is the reason why the processing terminates if the latest measurement result A is not an after-meal data. In the case that HbA1c is less than 9%, it is the present situation that it is not possible to find out a significant correlation between HbA1c and the urine sugar value measured in a condition other than the after-meal.

If the latest measurement is after-meal, all after-meal measured urine sugar values obtained during a past predetermined short period of time, for example, during the past one week, including the latest measurement result A of the urine sugar value, are read out and then an averaged value X is calculated. Furthermore, all after-meal measured urine sugar values obtained during a past predetermined long period of time, for example, during the past one month, are read out and then an averaged value Y is calculated. By comparing the averaged value X of the measured values obtained during the past predetermined short period of time (past one week) with the averaged value Y of the measured values obtained during the past predetermined long period of time (past one month), a ratio {X/Y} is calculated. When the ratio X/Y is not greater than 0.5, it is discriminated that HbA1c was improved not less than a predetermined value, for example, not less than 0.5%. On the other hand, when the ratio X/Y is not less than 2, it is discriminated that HbA1c was deteriorated not less than a predetermined value, for example, not less than 0.5%. In the case of 0.5<{X/Y}<2, it is considered that the change is less than 0.5%, and therefore, it is discriminated that there is neither significant improvement nor significant deterioration.

(4) If the latest HbA1c is not less than 9%, irrespectively of whether or not the latest measurement result A of the urine sugar value is an after-meal data, all measured urine sugar values obtained during a past predetermined short period of time, for example, during the past one week, are read out and then an averaged value X is calculated. Furthermore, all measured urine sugar values obtained during a past predetermined long period of time, for example, during the past one month, are read out and then an averaged value Y is calculated. By comparing the averaged value X of the measured values obtained during the past predetermined short period of time (past one week) with the averaged value Y of the measured values obtained during the past predetermined long period of time (past one month), a ratio {X/Y} is calculated. When the ratio X/Y is not greater than 0.5, it is discriminated that HbA1c was improved not less than a predetermined value, for example, not less than 0.5%. On the other hand, when the ratio X/Y is not less than 2, it is discriminated that HbA1c was deteriorated not less than a predetermined value, for example, not less than 0.5%. In the case of 0.5<{X/Y}<2, it is considered that the change is less than 0.5%, and therefore, it is discriminated that there is neither significant improvement nor significant deterioration.

Figure 7:
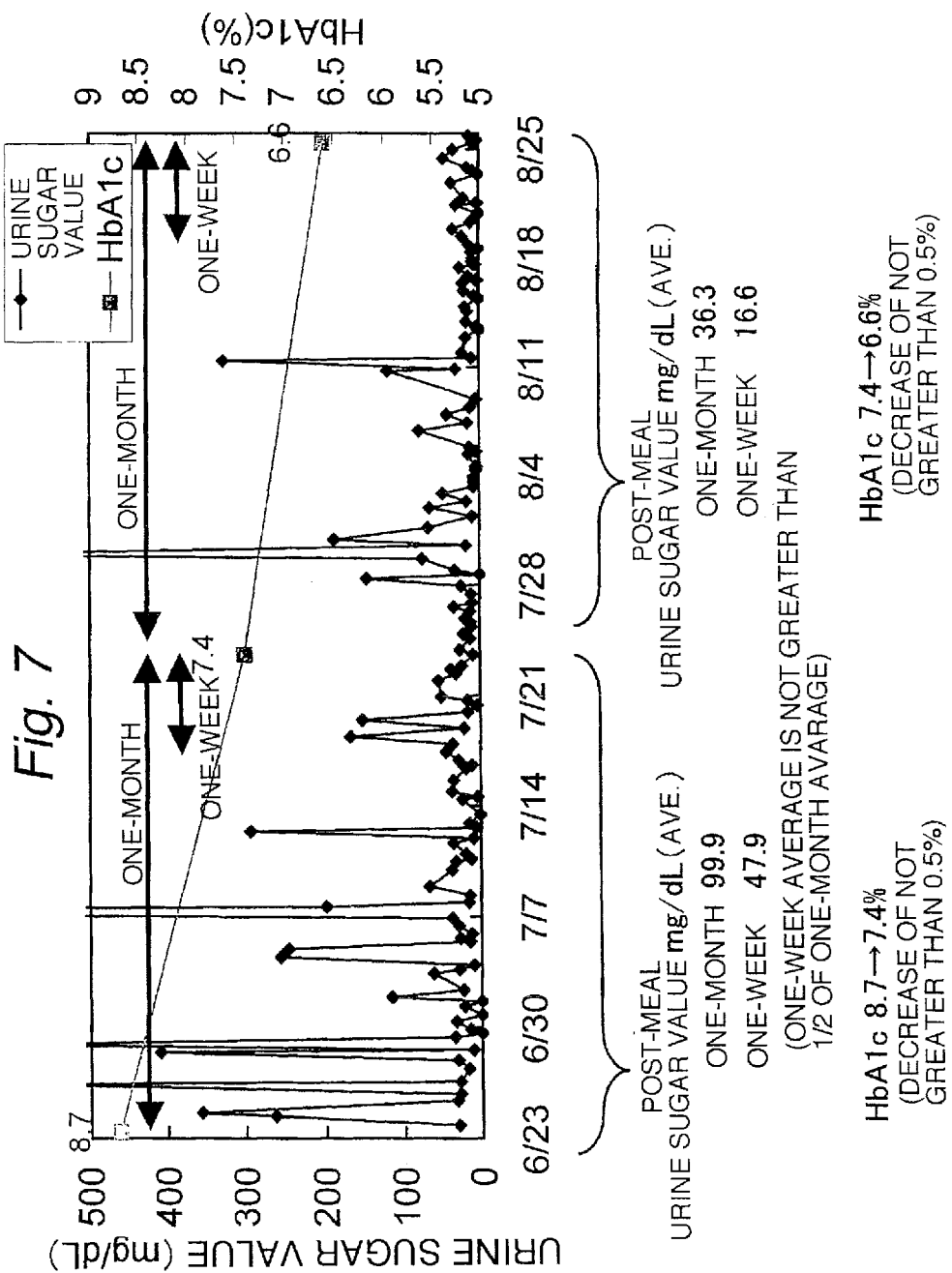
FIG. 7 is a graph showing an experimental data, testifying the blood sugar condition estimation method in accordance with the Embodiment 4 of this invention.

FIG. 7 is the experimental data which has verified the Embodiment 3 mentioned above. The graph of FIG. 7 illustrates the urine sugar values of a reagent measured after every meals over about two months, and HbA1c (%) measured monthly (three times for two months) in time sequence (the axis of ordinates:the urine sugar values and HbAc, and the axis of abscissas:day).

In addition, a lower portion of FIG. 7 explains the validity of the estimation concluding from comparison of the urine sugar values that HbA1c (%) was improved in a first one month and in a second one month of the two-month measurement period, respectively.

That is to say, from the measured values of the urine sugar value measured during the first one month, it is observed that the averaged value Y for the one month concerned is 99.9 (mg/dL), and the averaged value X for the final one week of the one month concerned is 47.9 (mg/dL). According to the Embodiments 3 of this invention, since [47.9<(99.9/2)], hence, since the averaged value X is not greater than ½ of the averaged value Y, it is discriminated that HbA1c (%) was improved not less than 0.5%. Here, focusing the actual measured value of HbA1c (%), the HbA1c (%) has decreased from 8.7% to 7.4%, namely, HbA1c (%) was improved not less than 0.5%. This verifies the validity of the Embodiment 3.

In the second one month, it can be said to be similar. That is to say, from the measured values of the urine sugar value measured during the second one month, it is observed that the averaged value Y for the one month concerned is 36.3 (mg/dL), and the averaged value X for the final one week of the one month concerned is 16.6 (mg/dL). According to the Embodiments 3 of this invention, since [16.6<(36.3/2)], hence, since the averaged value X is not greater than ½ of the averaged value Y, it is discriminated that HbA1c (%) was improved not less than 0.5%. Here, focusing the actual measured value of HbA1c (%), the HbA1c (%) has decreased from 7.4% to 6.6%, namely, HbA1c (%) was improved not less than 0.5%. This also verifies the validity of the Embodiment 3.

Here, in order to verify from comparison of the monthly measured HbA1c (%) (three times for two months), the actual measured value of HbA1c (%) was examined by dividing the two months into a first one month and a second one month. However, it would be understood from the explanation of the Embodiment 3 mentioned above that attention is not necessarily paid to only one month before the measurement date of HbA1c in the Embodiment 3. For example, when the urine sugar value was measured on Aug. 11, 2008 in the graph of FIG. 7, the HbA1c estimation is carried out from the measured values of the urine sugar values in one week and in one month just before Aug. 11, 2008. The averaged value Y for one month before Aug. 11, 2008 is 64.2 (mg/dL), and the averaged value X for one week before Aug. 11, 2008 is 36.6 (mg/dL). According to Embodiment 3 of this invention, since [(64.2/2)<36.6<2(64.2)], hence, the averaged value X is greater than ½ of the averaged value Y but less than two times the averaged value Y. Therefore, it is discriminated that the change is not greater than 0.5%, namely, that there is neither significant improvement nor significant deterioration.

In the graph of FIG. 7, if the HbA1c estimation was carried out every day after a daily measurement of the urine sugar value during the second one month, there is obtained either the discrimination result that "HbA1c (%) was improved not less than 0.5%" or the discrimination result that "there is neither significant improvement nor significant deterioration". Accordingly, a diabetic can recognize that HbA1c is in an improving tendency. It could be seen that this recognition is consistent with the change of the measured value of HbA1c.

In Embodiment 3 mentioned above, the predetermined long period of time and the predetermined short period of time are one month and one week, respectively, but, are not limited to those specific periods of time. Generally, since the averaged value of the blood sugar values over one to two months is considered to indicate the blood sugar condition which is not influenced by a temporary change caused by meal and others, the predetermined long period of time is preferably set within the range of over one to two months, as a period presenting the urine sugar condition corresponding to the blood sugar condition. On the other hand, the predetermined short period of time corresponds to a period which presents a recent blood sugar condition but absorbs daily extreme variations. Therefore, the predetermined short period of time is preferably set within a range of not greater than one month, and is required to be sufficiently shorter than the predetermined long period of time. Accordingly, the predetermined short period of time is sufficiently shorter than the predetermined long period of time and is preferred to be at least not shorter than five days but not longer than two weeks. The predetermined long period of time is longer than at least two times the predetermined short period of time, and can be arbitrarily selected from the range of not shorter than two weeks but not longer than two months.

In addition, as regards the degree of improvement of the estimated HbA1c (%), the improvement of HbA1c of not less than a predetermined value is exemplified as the improvement of HbA1c of not less than 0.5%". However, this predetermined value is in no way limited to 0.5%, but may be any value which can be considered to show a significant improvement.

Furthermore, in the above mentioned embodiment, whether the extent of measured values for obtaining the averaged value is limited to only the after-meal measured values or includes all the measured values, is determined depending upon whether or not the latest HbA1c is less than 9%. However, this is based on the result of research of the inventor of this invention that when the boundary value of HbA1c was 9%, the result of discrimination is the highest in validity. Therefore, it is not absolute that the boundary value of HbA1c is 9%. Accordingly, it is considered that even if the boundary value of HbA1c is changed to a value larger or smaller than 9% but near to 9%, the validity of the result of discrimination will never abruptly drop. Therefore, the boundary value of HbA1c can be changed to a value larger or smaller than 9% but near to 9%,

Embodiment 5

Target Value Setting Function

In order to improve HbA1c (blood sugar condition, lifestyle habit), an improvement target is set, and whether or not the improvement target has been achieved is discriminated from the latest (recent) urine sugar data.

For example, when an improvement target is set to be an improvement of HbA1c of not less than 0.5%, the improvement target value is set to a half of an averaged value of urine sugar values in the past one month (measured at the same timing as the timing of the latest measurement) including the latest measured value. The latest measured value is compared with the improvement target value, and when the latest measured value exceeds the improvement target value, it is notified by for example a lamp or an alarm. Here, the one month is a predetermined period of time, which is in no way limited to the one month but can be arbitrarily selected from the range of not less than two weeks but not greater than two months.

Figure 8:
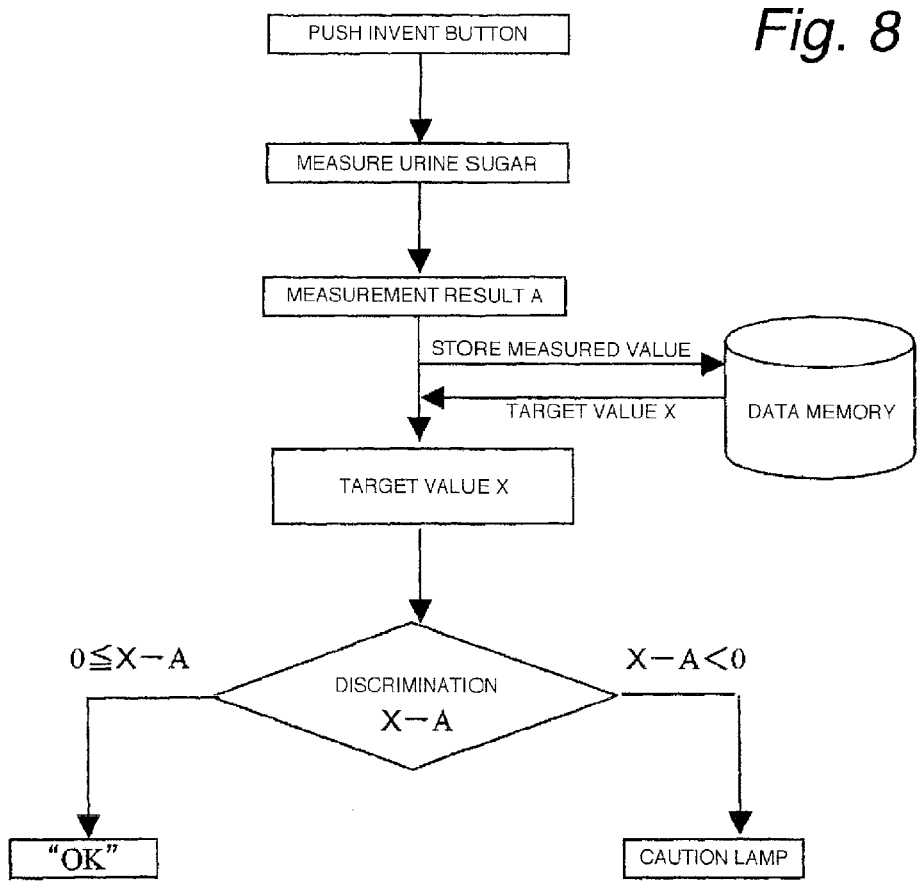
FIG. 8 is a flowchart illustrating the procedure of the blood sugar condition estimation method in accordance with the Embodiment 5 of this invention.

FIG. 8 is a flowchart illustrating the procedure of Embodiment 4 (target value setting function).

First of all, the improvement target, for example, "improvement of HbA1c of not less than 0.5%", is written and stored in the auxiliary memory 37 of the microcomputer 32 of the urine sugar meter.

In the meanwhile, the measurement data of the urine sugar values of at least the past one month is stored together with respective measurement timings in the auxiliary memory 37 of the microcomputer 32.

(1) At each time the urine sugar is measured by the urine sugar meter 1, the measurement result A is stored in the auxiliary memory 37 of the microcomputer 32.

At each time the measurement result A of the urine sugar value is stored in the auxiliary memories 37 of the microcomputers 32, urine sugar measured values in the past one week including the latest measurement result A of the urine sugar value and measured for example at the same timing as the timing of the latest measurement result A of the urine sugar value, are read out, and an averaged value X is calculated, so that the averaged value X thus obtained is set as a target value. The latest measurement result A of the urine sugar value is compared with the target value, namely, the averaged value X thus obtained. If {X−A} is not less than 0 (zero), the "decrease" of the display unit of FIG. 4 is lit in order to indicate the achievement of the improvement target, "OK". Otherwise, both of "no change" and "increase" of the display unit of FIG. 4 are lit or blinked as "caution lamp".

In all the above mentioned embodiments, the data processing is carried out in the urine sugar meter itself. However, it is a matter of course that it is possible to carry out the data processing and to display the result of the date processing in a personal computer connected to the urine sugar meter. For example, as shown in FIG. 9, at each measurement, the urine sugar meter is connected with the personal computer, and the measured value and its measurement date and time data are transferred to the personal computer so as to be stored in a memory of the personal computer. In the meanwhile, when HbA1c was measured, the value of HbA1c and its measurement date and time data are inputted into the personal computer so as to be stored in a memory of the personal computer. A program previously installed in the personal computer for carrying out the procedures of Embodiments 1 to 4 mentioned above, is selectively executed so that the result of the procedures of Embodiments 1 to 4 can be obtained by use of the personal computer. This will be apparent to averaged persons skilled in the art with no necessity of explanation.

As described above, the blood sugar condition estimation method and apparatus of this invention has the function to store a measured urine sugar value and the value of HbA1c inputted together with its measurement date and time, and can carry out the discrimination of the blood sugar condition and the estimation of HbA1c, etc. on the basis of a non-invasive urine sugar measurement.

Specifically, the blood sugar condition estimation method and apparatus of this invention can discriminate the improvement or deterioration of HbA1c by comparing the measured urine sugar value with past measured urine sugar values.

In addition, the blood sugar condition estimation method and apparatus of this invention can discriminate, on the basis of the measured urine sugar value, whether or not the present lifestyle improving effort will lead to the improvement of HbA1c.

Furthermore, the blood sugar condition estimation method and apparatus of this invention can calculate a urine sugar target value from the measured urine sugar value and the improvement target value of HbA1c.

Since the blood sugar condition estimation method and apparatus of this invention stores a measured urine sugar value and the value of HbA1c inputted, it is possible to easily select out the discrimination, the estimation and the setting of the target value, which can be obtained by utilizing the stored data. In addition, for the discrimination, the estimation and the setting of the target value, an optimum calculation method can be selected from the purpose, the stage of diabetes of the user, the life pattern, etc.

Therefore, just after the measurement, the blood sugar condition estimation method and apparatus of this invention can discriminate a "good or bad" in connection with meal, exercise, etc. just before the measurement, and also, can estimate the improving tendency of HbA1c. Furthermore, since the improvement target can be set, it is possible to sustain the user's motivation for the user's blood sugar control.

Moreover, if the urine sugar meter, which is the blood sugar condition estimation method and apparatus of this invention, is added with communication means, it is possible to combine with data obtained by further various external instruments (for example, the record of body weight, meal and exercise, etc.), with the result that the reliability of the discrimination, the estimation and the target setting is elevated.

Furthermore, if the data obtained is accumulated into a server through Internet, etc., the reliability of the discrimination, the estimation and the target setting is elevated. If the urine sugar meter stands alone, those are calculated on the basis of the data of only the single user. If the urine sugar meter is connected to an external server, since all data of the urine sugar meter's users is accumulated, even if the data of only the single user is less, the estimation becomes easy so that the reliability of the discrimination is elevated.

The invention claimed is:

1. A urine sugar condition estimation method, comprising the steps of:
 (1) measuring a urine sugar value A;
 (2) obtaining an averaged value X of measured urine sugar values measured during a past predetermined period of time, always including all measured urine sugar values measured at the same timing in a one-day life as the timing when said latest measured the urine sugar value A is measured;
 (3) discriminating whether or not said measured urine sugar value A is less than a discriminating method classification boundary value;

(4) when the measured urine sugar value A is less than the discriminating method classification boundary value, calculating a difference between said averaged value X and said measured urine sugar value A;
(5) when said difference {X−A} is not less than a positive discriminating reference difference, discriminating as being a urine sugar value decrease;
(6) when the measured urine sugar value A is not less than the discriminating method classification boundary value, calculating a ratio between said measured urine sugar value A and said averaged value X; and,
(7) when said ratio {A/X} is not greater than a first discriminating reference ratio, discriminating as being the urine sugar value decrease.

2. A urine sugar condition estimation method claimed in claim 1, further comprises the steps of:
(8) when said difference {X−A} is not greater than a negative discriminating reference difference, discriminating as being a urine sugar value increase;
(9) when said difference {X−A} is greater than said negative discriminating reference difference but less than said positive discriminating reference difference, discriminating as being no change in the urine sugar value;
(10) when said ratio {A/X} is not less than a second discriminating reference ratio, discriminating as being the urine sugar value increase; and
(11) when said ratio {A/X} is greater than said first discriminating reference ratio but less than said second discriminating reference ratio, discriminating as being no change in the urine sugar value.

3. A urine sugar condition estimation method claimed in claim 2, wherein said discriminating method classification boundary value is 50 mg/dL, and said positive discriminating reference difference is 10 mg/dL, said negative discriminating reference difference is −10 mg/dL, said first discriminating reference ratio is 0.8, and said second discriminating reference ratio is 1.2.

4. A urine sugar condition estimation method claimed in claim 3, wherein said predetermined period of time is selected from a range of five days from five weeks.

5. A blood sugar state estimation method, comprising the steps of:
(1) measuring a urine sugar value A;
(2) obtaining an averaged value X of measured urine sugar values measured during a past predetermined period of time, always including all measured urine sugar values measured at the same timing in a one-day life as the timing when said latest measured urine sugar value A was measured;
(3) discriminating whether or not said measured urine sugar value A is less than a discriminating method classification boundary value;
(4) when the measured urine sugar value A is less than the discriminating method classification boundary value, calculating a difference between said averaged value X and said measured urine sugar value A;
(5) when said difference {X−A} is not less than a positive discriminating reference difference, discriminating as being a blood sugar value decrease;
(6) when the measured urine sugar value A is not less than the discriminating method classification boundary value, calculating a ratio between said measured urine sugar value A and said averaged value X; and,
(7) when said ratio {A/X} is not greater than a first discriminating reference ratio, discriminating as being the blood sugar value decrease.

6. A blood sugar state estimation method claimed in claim 5, further comprises the steps of:
(8) when said difference {X−A} is not greater than a negative discriminating reference difference, discriminating as being a blood sugar value increase;
(9) when said difference {X−A} is greater than said negative discriminating reference difference but less than said positive discriminating reference difference, discriminating as being no change in the blood sugar value;
(10) when said ratio {A/X} is not less than a second discriminating reference ratio, discriminating as being the blood sugar value increase; and
(11) when said ratio {A/X} is greater than said first discriminating reference ratio but less than said second discriminating reference ratio, discriminating as being no change in the blood sugar value.

7. A blood sugar condition estimation method claimed in claim 6, wherein said discriminating method classification boundary value is 50 mg/dL, and said positive discriminating reference difference is 10 mg/dL, said negative discriminating reference difference is −10 mg/dL, said first discriminating reference ratio is 0.8, and said second discriminating reference ratio is 1.2.

8. A blood sugar condition estimation method claimed in claim 7, wherein said predetermined period of time is selected from a range of five days from five weeks.

9. A blood sugar state estimation method, comprising the steps of:
(1) measuring a urine sugar value A;
(2) discriminating whether or not the latest HbA1c is less than a discriminating method classification boundary value;
(3) when said latest HbA1c is less than said discriminating method classification boundary value, if said latest measured urine sugar value A was measured after a meal, obtaining an averaged value X of all post-meal measured urine sugar values measured during a past predetermined short period of time including said latest measured urine sugar value A and an averaged value Y of all post-meal measured urine sugar values measured during a past predetermined long period of time;
(4) comparing said averaged value X of the measured urine sugar values measured during said past predetermined short period of time with said averaged value Y of the measured urine sugar values measured during said past predetermined long period of time, and discriminating that a significant improvement is found if the ratio {X/Y} is not greater than a first reference value;
(5) when said latest HbA1c is not less than said discriminating method classification boundary value, obtaining an averaged value X of all measured urine sugar values measured during said past predetermined short period of time including the latest measured urine sugar value A and an averaged value Y of all measured urine sugar values measured during said past predetermined long period of time;
(6) comparing said averaged value X of the measured urine sugar values measured during said past predetermined short period of time with said averaged value Y of the measured urine sugar values measured during said past predetermined long period of time, and discriminating that a significant improvement is found if the ratio {X/Y} is not greater than said first reference value.

10. A blood sugar state estimation method claimed in claim 9, further comprises the steps of:

(7) when said ratio {X/Y} is not less than a second discriminating reference ratio, discriminating that a significant deterioration is found; and (8) when said ratio {X/Y} is greater than said first discriminating reference ratio but less than said second discriminating reference ratio, discriminating that neither the significant improvement nor the significant deterioration is found.

11. A blood sugar state estimation method claimed in claim 10, wherein said predetermined short period of time is not less than five days but not greater than two weeks, and said predetermined long period of time is at least two times said predetermined short period of time, and is not less than two weeks but not greater than two months.

12. A blood sugar state estimation method claimed in claim 10, wherein said predetermined short period of time is one week and said predetermined long period of time is one month.

13. A blood sugar state estimation method claimed in claim 11, wherein said discriminating method classification boundary value of HbA1c is 9%.

14. A blood sugar condition estimation method comprising the steps of:

(1) measuring a urine sugar value A;

(2) obtaining an averaged value X of measured urine sugar values, including the latest measured urine sugar value A, measured during a past predetermined period of time at the same timing as the timing when said latest measured urine sugar value A was measured, and considering the averaged value X thus obtained as a target value;

(3) comparing said target value, namely, said averaged value X with said latest measured urine sugar value A, and discriminating that an improvement target is achieved when the difference {X−A} is not less than 0 (zero).

* * * * *